United States Patent [19]

Borghi et al.

[11] Patent Number: 5,135,857

[45] Date of Patent: Aug. 4, 1992

[54] PROCESS FOR THE PREPARATION OF DE-MANNOSYL TEICOPLANIN DERIVATIVES

[75] Inventors: Angelo Borghi, Palestrina; Giancarlo Lancini, Vittadini; Piero Antonini, Mazzini, all of Italy

[73] Assignee: Gruppo Lepetit S.p.A., Milan, Italy

[21] Appl. No.: 729,512

[22] Filed: Jul. 12, 1991

Related U.S. Application Data

[60] Division of Ser. No. 655,252, Feb. 13, 1991, Pat. No. 5,064,810, which is a continuation of Ser. No. 211,955, Jun. 27, 1988, abandoned.

[30] Foreign Application Priority Data

Jul. 3, 1987 [GB] United Kingdom ............... 8715735

[51] Int. Cl.$^5$ .................... C07K 7/54; C12P 21/04; C12R 1/465; C12R 1/365
[52] U.S. Cl. .................... 435/71.3; 435/71.1; 435/71.2; 435/872; 435/886; 514/9; 530/317
[58] Field of Search ............ 435/71.171.2, 71.3, 435/253.5, 253.2, 886, 872

[56] References Cited

U.S. PATENT DOCUMENTS

| | | | |
|---|---|---|---|
| 4,927,754 | 5/1990 | Assi et al. | 435/71.3 |
| 4,935,238 | 6/1990 | Selva et al. | 435/170 |
| 4,954,483 | 9/1990 | Malabarba et al. | 530/317 |
| 4,994,555 | 2/1991 | Panzone et al. | 435/71.3 |
| 5,064,811 | 11/1991 | Borghi et al. | 514/9 |
| 5,085,990 | 2/1992 | Lancini | 435/252.6 |

*Primary Examiner*—Herbert J. Lilling
*Attorney, Agent, or Firm*—J. Michael Dixon

[57] ABSTRACT

The object of this invention are de-mannosylated teicoplanin derivatives which can be obtained in good yield by microbiological transformation with cultures of *Nocardia orientalis* NRRL 2450 or *Streptomyces candidus* NRRL 3218.

3 Claims, No Drawings

PROCESS FOR THE PREPARATION OF DE-MANNOSYL TEICOPLANIN DERIVATIVES

This is a divisional of application Ser. No. 07/655,252, filed Feb. 13, 1991 now U.S. Pat. No. 5,069,810 which is a continuation of Ser. No. 07/211,955, filed Jun. 27, 1988, now abandoned.

The object of this invention are antibiotic de-mannosyl teicoplanin derivatives of the formula

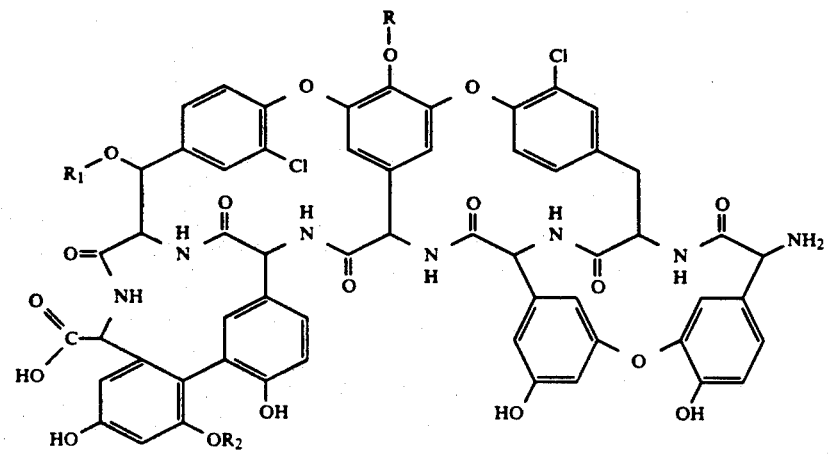

(I)

wherein
R is N-(Z-4-decenoyl)-beta-D-2-deoxy-2-amino-glucopyranosyl, N-(8-methyl-nonanoyl)-beta-D-2-deoxy-2-amino-glucopyranosyl, N-decanoyl-beta-D-2-deoxy-2-amino-glucopyranosyl, N-(8-methyl-decanoyl)-beta-D-2-deoxy-2-amino-glucopyranosyl, N-(9-methyldecanoyl)-beta-D-2-deoxy-2-amino-glucopyranosyl;
$R_1$ is N-acetyl-beta-D-2-deoxy-2-amino-glucopyranosyl;
$R_2$ is hydrogen,
their addition salts with acids and bases and any mixture thereof, in any proportion.

A further object of this invention is a process for the obtention of said antibiotic derivatives from the corresponding mannosylated teicoplanin precursors.

Teicoplanin is an antibiotic produced by cultivating the strain *Actinoplanes teichomyceticus* nov. sp. ATCC 31121 in a culture medium containing assimilable sources of carbon, nitrogen and inorganic salts.

The main product resulting from the above mentioned strain was a mixture of three main factors ($A_1$, $A_2$ and $A_3$) originally referred to as teichomycin U.S. Pat. No. 4,239,751).

The more recent teicoplanin preparations obtained by purification of the product recovered from the fermentation broth and suitable for chemotherapeutic use in the treatment of infections caused by gram-positive organisms (H. H. Williams et al.: Journal of Hospital Infection (1986), 7 (Supplement A), 101-103) contain as the major component a complex of five structurally closely related substances which had been originally referred to, as whole, as teichomycin factor $A_2$. The above mentioned five closely related substances have been successively isolated and characterized as single components of the complex which was then currently designated and referred to in the scientific papers and patent literature as "teicoplanin $A_2$" or "teicoplanin complex".

The five major components of teicoplanin complex (conventionally named: TA2-1, TA2-2, TA2-3, TA2-4 and TA2-5) may be represented by the above general formula (I) above wherein:
R respectively is:
TA2-1): N-(Z-4-decenoyl)-beta-D-2-deoxy-2-amino-glucopyranosyl;
TA2-2): N-(8-methyl-nonanoyl)-beta-D-2-deoxy-2-aminoglucopyranosyl;
TA2-3): N-decanoyl-beta-D-2-deoxy-2-amino-glucopyranosyl;
TA2-4): N-(8-methyl-decanoyl)-beta-D-2-deoxy-2-aminoglucopyranosyl;
TA2-5): N-(9-methyl-decanoyl)-beta-D-2-deoxy-2-aminoglucopyranosyl;
$R_1$ is N-acetyl-beta-D-2-deoxy-2-amino-glucopyranosyl;
$R_2$ is alpha-D-mannopyranosyl.

Their respective ratios in the teicoplanin complex can vary according to the fermentation conditions and the precursors added to the fermentation medium as described in the E.P.A. publication No. 204179.

In the prior art are described the aglycone of teicoplanin (L 17392), i.e. the compound of formula (I) above wherein $R = R_1 = R_2 =$ hydrogen, and two pseudo aglycones, namely compound L 17054 (formula I, R = hydrogen, $R_1 =$ N-acetyl-beta-D-2-deoxy-2-amino-glucopyranosyl, $R_2 =$ alpha-D-mannopyranosyl and compound L 17046 (formula I, $R = R_2 =$ hydrogen; $R_1 =$ N-acetyl-beta-D-2-deoxy-2-amino-glucopyranosyl).

The above mentioned derivatives of teicoplanin are obtained by submitting the teicoplanin complex or the individual major components thereof to appropriate acid hydrolysis conditions. See for instance: E.P.A. publication No. 146053, E.P.A. publication No. 119575 and E.P.A. No. 119574.

In summary, mild acid hydrolysis conditions displaces the acylglucosamine moiety, a stronger acidic treatment displaces the mannose unit and a further acidic treatment allows displacement of the remaining N-acetyl-glucosamine moiety yielding the aglycone.

De-mannosyl teicoplanin derivatives, i.e. teicoplanin derivatives where R and $R_1$ have the same meanings as in the teicoplanin complex represented above and $R_2$ is hydrogen have not been described so far and apparently, they cannot be obtained by acidic treatment. Basic treatment of teicoplanin leads to epimerization at the chiral center of the third aminoacid (starting from the N-terminus) with remarkable decrease of the activity (see J.C.J. Barna et al.: The Journal of Antibiotics 37, No. 10, page 1204–1208, 1984).

According to the present invention, de-mannosylated teicoplanin derivatives can be obtained in good yield by microbiological transformation of a substrate selected from teicoplanin complex, any mixture of the single components and a single component thereof with cultures of *Nocardia orientalis* NRRL 2450 or *Streptomyces candidus* NRRL 3218, their natural mutants or variants exhibiting the same property of splitting the glycosidic bond with the D-mannose moiety in the teicoplanin molecule, the washed mycelium or a cell-free preparation thereof.

The first above mentioned strain is also referred to in the recent literature as *Streptomyces orientalis* NRRL 2450 (see: S. K. Chung et al., The Journal of Antibiotics 39, No. 5, page 652–659, 1986).

Samples of said strains bearing our internal codes A/156 and S/802 respectively have been redeposited on Jun. 10, 1987 at the ATCC (American Type Culture Collection, 12301 Parklawn Drive, Rockville, Md. 20852 U.S.A.) under the conditions established by the Budapest Treaty on the International Recognition of the Deposit of Microorganisms for the Purposes of Patent Procedure where have been assigned the following ATCC numbers respectively 53630 and 53629.

When the teicoplanin complex or a mixture of its single components is used as a substrate for the microbiological transformation, the resulting product is a mixture of five de-mannosyl derivatives of the formula I above, in any proportion. Also these mixtures fall within the scope of this invention. Said mixtures can be used as such for the uses described herein or can be optionally separated into the five individual components by means of known techniques such as, for instance, reverse-phase partition, ion exchange chromatography or preparative HPLC (see for reference U.S. Pat. No. 4,542,018).

The de-mannosyl teicoplanin derivatives of this invention are antibiotically active compounds.

For the sake of brevity each de-mannosyl teicoplanin compound of this invention will be hereinafter indicated with a conventional name referring to the teicoplanin complex major component from which it derives, preceded by the acronym DM.

Accordingly:

DM-TA2-1 indicates the de-mannosyl derivative of component 1 (TA2-1);

DM-TA2-2 indicates the de-mannosyl derivative of component 2 (TA2-2);

DM-TA2-3 indicates the de-mannosyl derivative of component 3 (TA2-3);

DM-TA2-4 indicates the de-mannosyl derivative of component 4 (TA2-4);

DM-TA2-5 indicates the de-mannosyl derivative of component 5 (TA2-5).

The antibacterial activity of the compounds of the invention can be demonstrated in vitro by means of standard dilution tests on different microorganism cultures.

Culture media and growth conditions for MIC (minimal inhibitory concentration) determinations were as follows: Isosensitest broth (Oxoid), 24 h, for staphylococci, *Strep. faecalis* and Gram-negative bacteria (*Escherichia coli*); Todd-Hewitt broth (Difco), 24 h for other streptococcal species; GC base broth (Difco)+1% Isovitalex (BBL), 48 h, $CO_2$-enriched atmosphere for *Neisseria gonorrhoeae*; Brain Heart broth (Difco)+1% Supplement C (Difco), 48 h for *Haemophilus influenzae*; Inocula were of about $10^4$–$10^5$ colony-forming units/ml for broth dilution MICs.

The minimal inhibitory concentrations (MIC, microgram/ml) of the above de-mannosyl teicoplanin derivatives for some microorganisms are reported below in Table I.

TABLE I

| Strain | M.I.C. (microgram/ml) | | | |
|---|---|---|---|---|
| | DM-TA2-2 | DM-TA2-3 | DM-TA2-4 | DM-TA2-5 |
| *Staph. aureus* L165 | 0.063 | 0.063 | 0.125 | 0.063 |
| *Staph. aureus* ($10^6$ cfu/ml) | 0.125 | 0.125 | 0.25 | 0.125 |
| *Staph. aureuss* (30% bovine serum) | 0.5 | 0.5 | 0.5 | 0.5 |
| *Staph. epidermidis* L147 ATCC 12228 (coagulase negative) | 0.063 | 0.063 | 0.063 | 0.063 |
| *Strep. pyogenes* L49 C203 | 0.063 | 0.063 | 0.063 | 0.063 |
| *Strip. pneumoniae* L44 UC41 | 0.063 | 0.063 | 0.063 | 0.063 |
| *Strep. faecalis* L149 ATCC 7080 | 0.063 | 0.063 | 0.063 | 0.063 |
| *Strep. mitis* L796 (clinical isolate) | 0.063 | 0.063 | 0.125 | 0.063 |
| *Neisseria gonorrhoeae* L997 ISM68/126 | 32 | 32 | 32 | 32 |
| *Haemophilus influenzae* L970 type b ATCC 19418 | 64 | 64 | 64 | 32 |
| *Escherichia coli* L47 SKF 12140 | >128 | >128 | >128 | >128 |
| *Proteus vulgaris* L79 X19H ATCC 881 | >128 | >128 | >128 | >128 |
| *Pseudomonas aeruginosa* L4 ATCC 10145 | >128 | 128 | >128 | >128 |
| *Staph. haemolyticus* L602 (clinical isolate) | 0.5 | 0.5 | 0.5 | 0.25 |

The de-mannosyl teicoplanin derivatives possess acid and basic functions and can form salts with organic and inorganic counter ions according to conventional procedures.

Representative and suitable acid addition salts of the compounds of the invention include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and the like acids.

Representative examples of bases are: alkali metal or alkaline-earth metal hydroxide such as sodium, potassium, calcium, magnesium, barium hydroxide; ammonia and aliphatic, alicyclic or aromatic organic amines such as methylamine, dimethylamine, trimethylamine, and picoline.

The transformation of the "non-salt" compounds of the invention into the corresponding addition salts, and the reverse, i.e. the transformation of an addition salt of a compound of the invention into the non-salt form, are within the ordinary technical skill and are encompassed by the present invention.

For instance, de-mannosyl teicoplanin derivatives can be transformed into the corresponding acid or base addition-salt by dissolving the non-salt form in an aqueous solvent and adding a slight molar excess of the selected acid or base. The resulting solution or suspension is then lyophilized to recover the desired salt.

In case the final salt is insoluble in a solvent where the non-salt form is soluble it is recovered by filtration from the organic solution of the non-salt form after addition of the stoichiometric amount or a slight molar excess of the selected acid or base.

Examples of these insoluble salts are calcium, magnesium and barium salts.

The non-salt form can be prepared from a corresponding acid or base salt dissolved in an aqueous solvent which is then neutralized to free the non-salt form.

When following the neutralization the elimination of the excess of acid or base is necessary, a common desalting procedure may be employed.

For example, column chromatography on silanised silica gel, non-functionalized polystyrene, acrylic and controlled pore polydextrane resins (such as Sephadex LH 20) or activated carbon may be conveniently used. After eluting the undesired salts with an aqueous solution, the desired product is eluted by means of a linear gradient or a step-gradient of a mixture of water and a polar or apolar organic solvent, such as acetonitrile/water from 50:50 to about 100% acetonitrile.

As it is known in the art, the salt formation either with pharmaceutically acceptable acids (or bases) or non-pharmaceutically acceptable acids (or bases) may be used as a convenient purification technique. After formation and isolation, the salt form of a de-mannosyl teicoplanin antibiotic can be transformed into the corresponding non-salt form or into a pharmaceutically acceptable salt form.

The de-mannosyl teicoplanin derivatives of this invention are prepared by submitting a substrate selected from teicoplanin complex, any mixture of the single components and a single component thereof which can be represented by the general formula I above wherein: R respectively is:

TA2-1): N-(Z-4-decenoyl)-beta-D-2-deoxy-2-aminoglucopyranosyl;
TA2-2): N-(8-methyl-nonanoyl)-beta-D-2-deoxy-2-aminoglucopyranosyl;
TA2-3): N-decanoyl-beta-D-2-deoxy-2-aminoglucopyranosyl;
TA2-4): N-(8-methyl-decanoyl)-beta-D-2-deoxy-2-aminoglucopyranosyl;
TA2-5): N-(9-methyl-decanoyl)-beta-D-2-deoxy-2-aminoglucopyranosyl;
$R_1$ is N-acetyl-beta-D-2-deoxy-2-amino-glucopyranosyl;
$R_2$ is alpha-D-mannopyranosyl
to a microbiological transformation with a microorganism selected from strain *Nocardia orientalis* NRRL 2450, *Streptomyces candidus* NRRL 3218, the natural variants and mutants thereof exhibiting the same property of splitting the glycosidic bond with the D-mannose moiety in the teicoplanin molecule, the washed mycelium and a cell-free preparation thereof.

According to a preferred embodiment of this invention, the selected starting material either in pure form or in the form of any crude preparation thereof, including harvested fermentation broth from *Actinoplanes teichomyceticus* nov. sp. ATCC 31121, is contacted with a growing culture of one of the above strains under fermentation conditions.

The above mentioned strains are cultivated under usual submerged aerobic conditions in a medium containing assimilable sources of carbon, nitrogen and inorganic salts.

Generally, the starting material mentioned above can be added to a culture of *Nocardia orientalis* NRRL 2450 or *Streptomyces candidus* NRRL 3218, at a time varying from 18 hours from the inoculation time to the time at which the culture has reached its maximum growth, however, addition after 24-72 hours from inoculation is, at least in some instances, preferred.

The reaction time, i.e. the time of exposure of the starting material to the microbial culture before recovering the final product, may vary between 48 and 140 hours, depending on the specific conditions employed. Anyway, since the reaction can be monitored as known in the art, for instance by following the decrease of the starting material and/or the increase of the final product by HPLC, the skilled man is capable of readily determine when the reaction is to be considered as complete and the recovery procedure can be started.

Instead of employing a growing culture of *Nocardia orientalis* NRRL 2450 or *Streptomyces candidus* NRRL 3218, one may employ a culture of any mutant or variant thereof which is still capable of splitting the glycosidic bond between the phenolic moiety and the mannose portion of the above mentioned starting material to give the de-mannosylated compounds of the invention. Any process according to the present invention which employs any such mutant or variant, is considered to be encompassed by the scope of the present invention.

Moreover, the compounds of the present invention can be prepared according to the method of the invention by using a mycelium of the above identified de-mannosylating microorganism culture, washed in an isotonic saline solution, conveniently NaCl, in order not to disrupt said aqueous solution of mycelium.

After having washed the mycelium, it is conveniently resuspended in a physiologically acceptable medium. The washed mycelium procedure can be used in order to increase the amounts of teicoplanin compounds to be reacted while maintaining optimal yields. It is also possible to carry out a cell-free preparation obtained by disrupting the cells, e.g. by sonication.

The recovery of the antibiotic substances from the reaction medium is then conducted according to known per se techniques which include extraction with solvents, precipitation by adding non-solvents or by changing the pH of the solution, partition chromatography, reverse-phase partition chromatography, ion-exchange chromatography, affinity chromatography and the like.

A preferred procedure includes an affinity chromatography on immobilized D-Alanyl-D-Alanine followed by separation at different pH.

Immobilized D-Alanyl-D-Alanine matrices suitable for the present recovery process are disclosed in European Patent Application Publication No. 122969. The preferred matrix in this recovery process is D-Alanyl-D-Alanine coupled with a controlled pore cross-linked polydextrane.

The reaction medium can be subjected to the affinity chromatography directly after filtration or after a preliminary purification procedure. This latter procedure includes making the whole medium basic, preferably between pH 8.5 and 11 and then filtering in the presence of a filter aid, if convenient.

The clear filtrate is then adjusted to a pH value between 7 and 8 and then subjected to an affinity chromatography on immobilized D-Alanyl-D-Alanine, either in column or batchwise.

While the binding of the substance to the affinity matrix is preferably made at a pH of about 7.0–8.0, its elution is performed at more basic pH values (preferably between 9.0 and 10.5) by means of an aqueous base. This aqueous base may be ammonia, a volatile amine, an alkali or alkali metal hydroxide or a basic buffered solution optionally in the presence of a polar organic solvent such as a polar water-miscible solvent.

Representative examples of polar water-miscible solvents are: water-soluble alcohols, (such as methanol, ethanol, iso-propanol, n-butanol), acetone, acetonitrile, lower alkyl alkanoates (such as ethyl acetate), tetrahydrofuran, dioxane and dimethylformamide and mixtures thereof; the preferred polar water-miscible solvent being acetonitrile.

After removing the impurities by rinsing the column with aqueous buffer pH 4–9, optionally containing salts, (e.g. ammonium formate) urea and/or water-miscible solvents, the de-mannosyl teicoplanin antibiotic substance is eluted with the above eluting mixture. The eluate is analyzed by HPLC and the fractions containing the desired material are pooled together.

This eluate is adjusted to pH 7.0–7.5 with an organic or mineral acid.

The eluate is then submitted to concentration and desalting procedures.

A convenient desalting procedure includes applying the antibiotic containing aqueous solution to a silanised silica gel column, washing with distilled water and eluting with a mixture of a polar water-miscible solvent as defined above and water.

Alternatively, the aqueous solution of the de-mannosylated teicoplanin derivative(s) is submitted to simultaneous concentration/desaltion procedures by ultrafiltration through a ultrafiltration membrane with a nominal molecular weight limit (NMWL) of 1000 dalton or less.

The solution obtained from the above procedure is then lyophilized and the recovered material is submitted to further purification.

In some cases, in particular, for large scale preparations, it is preferred to carry out said purification in two steps. The first one is carried out according to a reverse phase chromatography general procedure already described in U.S. Pat. No. 4,542,018 for the separation of the individual factors of teicoplanin complex. According to a specific embodiment of said procedure, the de-mannosyl teicoplanin derivative(s) product obtained from lyophilization is dissolved in an ammonium formate/acetonitrile mixture and adjusted at pH 7.5 with sodium hydroxide and the obtained solution is passed through a silanised silica gel column and then the column is eluted with a linear gradient of acetonitrile in ammonium formate solution. The eluate is monitored by HPLC and the fractions containing the desired material(s) are pooled together and evaporated under reduced pressure yielding the solid material desired. This procedure is also useful for the separation of the single de-mannosyl derivatives of teicoplanin complex when this latter or a mixture of its single components is used as the starting material instead of the individual components.

The first purification step may be avoided when the starting material utilized for the microbiological transformation is sufficiently pure and essentially consists of an individual components of teicoplanin complex.

The second purification step involves a semi-preparative HPLC on a silanised chemically modified preparative HPLC column by using two mixtures of acetonitrile/ammonium formate in different ratios as mobile phases and maintaining a linear gradient of acetonitrile in ammonium formate. The eluted fractions are monitored by HPLC analysis and those containing the desired product are pooled together, the organic solvent is evaporated under reduced pressure and then the aqueous solution is submitted to simultaneous concentration/desaltion by ultrafiltration as described above. The solution resulting from ultrafiltration is then lyophilized yielding the desired pure product.

The de-mannosyl teicoplanin derivatives of this invention are active against gram-positive bacteria which are responsible for many widely diffused infections.

In particular, the compounds of this invention show a remarkable activity against *Staphylococcus epidermidis* and *Staphylococcus haemolyticus*.

In general, for the antibacterial treatment the de-mannosyl teicoplanin derivatives as well as the non-toxic pharmaceutically acceptable salts thereof or mixture thereof, can be administered by different routes such as topically or parenterally. The parenteral administration is, in general, the preferred route of administration.

Compositions for injection may take such forms as suspensions, solutions, or emulsions in oily or aqueous vehicles, and may contain adjuvants such as suspending, stabilizing and/or dispersing agents.

Alternatively, the active ingredient may be in powder form for reconstitution at the time of delivery when a suitable vehicle, such as sterile water, is added thereto.

Depending on the route of administration, these compounds can be formulated into various dosage forms.

In some instances, it may be possible to formulate the compounds of the invention in enteric-coated dosage forms for oral administration which may be prepared as known in the art (see for instance "Remington's Pharmaceutical Sciences", fifteenth edition, Mack Publishing Company, Easton, Pa., USA, page 1614).

This could be specially the case when the absorption of the antimicrobial substance in the enteric tract is particularly desired while passing unaltered through the gastric tract.

The amount of active principle to be administered depends on various factors such as the size and condition of the subject to be treated, the route and frequency of administration, and the causative agent involved.

The antibiotic substances of the present invention and the physiologically acceptable salts thereof, are generally effective at a daily dosage of between about 0.5 and 50 mg of active ingredient per kilogram of patient body weight, optionally divided into 1 to 4 administrations per day.

Particularly desirable compositions are those prepared in dosage units containing from about 50 to about 2,000 mg per unit.

Sustained-action formulations can be prepared based on different mechanisms and methods, as known in the art.

A preferred method for preparing a sustained-action formulation containing the de-mannosyl antibiotic substances, involves the use of a water insoluble form of the antibiotic suspended in an aqueous or oily medium.

Besides their activity as medicaments, the de-mannosyl antibiotics of this invention and the non-toxic salts thereof, can be used as animal growth promoters, i.e. to increase the feed efficiency of meat or milk producing animals.

For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and CO., S. Francisco, USA, 1969 or "Livestock Feeds and Feeding" O and B books, Corvallis, Oreg., USA, 1977) and are incorporated herein by reference.

DETAILED DESCRIPTION OF THE PREPARATION OF THE DE-MANNOSYL TEICOPLANIN DERIVATIVES

1. Preparation of de-mannosyl teicoplanin complex component 2 (DM-TA2-2)

A lyophilized tube containing *Nocardia orientalis* NRRL 2450 is open and aseptically transferred into a slant of oatmeal agar. After a 7 day incubation at 28° C., the culture is suspended in distilled water and inoculated into 2 Erlenmeyer flasks each containing 100 ml of vegetative medium S/bis having the following composition:

| Yeast extract | 4 g |
|---|---|
| Peptone | 4 g |
| Glucose | 10 g |
| MgSO$_4$ | 0.5 g |
| KH$_2$PO$_4$ | 2 g |
| K$_2$HPO$_4$ | 4 g |
| Distilled water to | 1000 ml |
| pH after sterilization: | 7 |

The inoculated medium is incubated 48 hours at 28° C. on a rotary shaker at 200 rpm. The resulting culture, subdivided in several portions of 5 ml each, is frozen and stored for further use.

A portion of 2.5 ml of the frozen stock culture is used to inoculate a 500 ml Erlenmeyer flask container 100 ml of vegetative medium S/bis. The culture was incubated at 20° C. for 48 h on a shaker at 200 rpm and 5 cm throw.

Five ml of this culture is used to inoculate 100 ml of productive medium C in a 500 ml flask having the following compositions:

| Glucose$^{(a)}$ | 2 g/l |
|---|---|
| Yeast extract | 5 g/l |
| Asparagine | 1.5 g/l |
| MgSO$_4$ | 0.5 g/l |
| CaCO$_3$ | 5 g/l |

| -continued | |
|---|---|
| NaCl | 0.1 g/l |
| CaCl$_2$.2H$_2$O | 0.1 g/l |
| Mineral supplement$^{(b)}$ | 1 ml/l |
| pH after sterilization: | 6.9 |

$^{(a)}$glucose was sterilized separately
$^{(b)}$mineral supplement composition:

| Boric acid | 0.50 g/l |
|---|---|
| CuSO$_4$.5H$_2$O | 0.04 g/l |
| KI | 0.10 g/l |
| FeCl$_3$.6H$_2$O | 0.20 g/l |
| MnSO$_4$.H$_2$O | 0.40 g/l |
| FeSO$_4$.7H$_2$O | 0.40 g/l |
| Ammonium molybdate | 0.20 g/l |

Thirty flasks are prepared according to the procedure described above.

After 48 hours, 20 mg of substrate TA2-2 (i.e. teicoplanin complex component 2) are added to each flask and the fermentation is continued aerobically for 72 hours from the addition time. HPLC analysis of the fermentation broth shows a 40 percent conversion of TA2-2 to DM-TA2-2.

The whole reaction medium from all thirty flasks is brought to pH 10.5 by addition of 1 N NaOH and then filtered in the presence of a filter aid. The pH of the filtered broth is adjusted to 7.5 by adding 1 N HCl and 150 ml of Sepharose-epsilon-aminocapropyl-D-Alanyl-D-Alanine affinity resin (EPA Publ. No. 122969) are added thereto.

The mixture is stirred overnight at 4° C. The resin was then separated from the exhausted broth and poured into a chromatographic column. The column was washed with five resin volumes of Tris-HCl buffer (0.05 M, pH 7.5) and then with the same volume of Tris base solution (0.05 M). The resin is eluted with a solution of 1% ammonium hydroxide by collecting several fractions of 100 ml each. Fractions were neutralized with formic acid and analyzed by HPLC. The HPLC analysis is carried out under the following conditions:

Instrument: Hewlett Packard model 1084 B with a 254 nm detector;

Column: Erbasil C-18, 5 micrometer, 4.6 ×150 mm;

Mobile phases: A) CH$_3$CN:NaH$_2$PO$_4$ (0.02 M), 5:95; B) CH$_3$CN:NaH$_2$PO$_4$ (0.02 M), 75:25;

| Gradient profile as follows: | | | | | |
|---|---|---|---|---|---|
| min | 0 | 40 | 45 | 48 | 50 |
| % B | 8 | 40 | 55 | 8 | stop |

Flow rate: 1.5 ml/min;

Injection: e.g. 20 microliter of a solution of the substance being examined at about 1 mg/ml in H$_2$O or H$_2$O:CH$_3$CN, 1:1.

Under the above conditions TA2-2 shows a retention time (Rt) of 24.71 min while DM-TA2-2 shows a RT of 26.30 minutes.

The fractions containing DM-TA2-2 are combined (about 200 ml) and then concentrated by ultrafiltration by using a 90 mm Hi-Flux U-F Cell Millipore apparatus supporting a PCAC Pellicon ultrafiltration membrane with a nominal molecular weight limit (NMWL) of 1000 dalton. The volume of the solution is reduced to about 20 ml and the residual is lyophilized giving 268 mg of crude DM-TA2-2.

The crude product is further purified by semi-preparative HPLC under the following conditions:

Apparatus: Waters liquid chromatograph, equipped with two pumps model 6000A, an adsorbance UV detector model 440 set at 254 nm and a solvent programmer model 660.

Column: HIBAR LiChrosorb RP-18, 7 micrometer, 250×10 mm (Merck);

Mobile phase:

A) aqueous (2 g/l) $HCOONH_4$/ $CH_3CN$ (9:1)

B) aqueous (2 g/l) $HCOONH_4$/ $CH_3CN$ (3:7);

Gradient: linear from 5% of B to 45% of B in 45 minutes;

Flow rate: 6 ml/min

Injection: 10 mg of product dissolved in 2 ml of A each time.

The portions of eluate which contain DM-TA2-2, identified through the chromatographic profile, are collected.

The above described semi-preparative purification is applied to the whole crude product recovered from ultrafiltration and the eluate portions are combined (180 ml as a whole) and the organic solvent is evaporated under vacuum. The remaining aqueous solution of DM-TA2-2 is concentrated by ultrafiltration under the same conditions to about 5 ml and the remaining solution is lyophilized yielding 85 mg of pure DM-TA2-2, i.e. the compound of formula I above wherein:

R = N-(8-methyl-nonanoyl)-beta-D-2-deoxy-2-amino-glucopyranosyl;

$R_1$ = N-acetyl-beta-D-2-deoxy-2-amino-glucopyranosyl;

$R_2$ = hydrogen.

The $^1$H-NMR spectrum of the pure DM-TA2-2 is recorded by using a Bruker model AM-250 instrument with an array processor, a magnet at 250 MHz, and a computerized console Aspect 3000. The spectra are obtained for protons in DMSO-$d_6$ solutions at 25° C. with TMS as reference.

The most significant signals of DM-TA2-2 in comparison with those of the teicoplanin complex are reported in Table II.

The Fast Atom Bombardment Mass Spectrum (FAB) of the pure DM-TA2-2 is recorded with a VG apparatus model 70-70 EQ equipped with FAB source. The positive ion spectra are obtained from the samples dispersed in a few microliters of alpha-thioglycerol, bombarded with a 7 KeV beam of Ar atoms. This experiment indicates a molecular of weight of 1715 which is consistent with the structure assigned.

In an experiment, carried out under the same conditions as above but replacing the strain *Nocardia orientalis* NRRL 2450 with strain Streptomyces candidus NRRL 3218, similar results are obtained.

2. Preparation of de-mannosyl teicoplanin complex component 3 (DM-TA2-3)

By operating with *Nocardia orientalis* NRRL 2450 as described in Preparation 1 but adding (after 48 hours from inoculum) as the substrate 200 mg of TA2-3 instead of TA2-2 a fermentation broth is obtained which is elaborated in the same manner as described under Preparation 1 above. Recovery and purification are carried out by following the same procedure as in Preparation 1. The conversion yield in the fermentation broth is 32 percent. The HPLC analysis performed under the same conditions as above shows RT values of 25.60 minutes for TA2-3 and of 27.20 minutes for DM-TA2-3 respectively. Yield 28 mg of pure DM-TA2-3, i.e. compound of formula (I) above wherein:

R = N-decanoyl-beta-D-2-deoxy-2-amino-glucopyranosyl;

$R_1$ = N-acetyl-beta-D-2-deoxy-2-amino-glucopyranosyl;

$R_2$ = hydrogen.

The NMR spectrum of pure DM-TA2-3 recorded under the same condition of Preparation 1 shows the characteristics signals indicated in Table II.

The FAB mass spectrum recorded under the same conditions as described under Preparation 1 shows a molecular weight of 1715 which is consistent with the structure assigned.

In an analogous experiment where *Nocardia orientalis* NRRL 2450 is replaced with *Streptomyces candidus* NRRL 3218 similar results are obtained.

3. Preparation of de-mannosyl teicoplanin complex component 4 (DM-TA2-4)

By operating with *Nocardia orientalis* NRRL 2450 as described in Preparation 1 but adding (after 72 hours from inoculum) as the substrate 200 mg of TA2-4 instead of TA2-2 a fermentation broth is obtained which is elaborated in the same manner as described under Preparation 1 above. The conversion yield in the fermentation broth is 34 percent. Recovery and purification are carried out by following the same procedure as in Preparation 1. The HPLC analysis performed under the same conditions as above shows RT values of 28.66 minutes for TA2-4 and of 30.19 minutes for DM-TA2-4 respectively. Yield 24 mg of pure DM-TA2-4, i.e. compound of formula (I) above wherein:

R = N-(8-methyl-decanoyl)-beta-D-2-deoxy-2-amino-glucopyranosyl;

$R_1$ = N-acetyl-beta-D-2-deoxy-2-amino-glucopyranosyl;

$R_2$ = hydrogen.

The NMR spectrum of pure DM-TA2-4 recorded under the same condition of Preparation 1 shows the characteristics signals indicated in Table II.

The FAB mass spectrum is recorded by using a Krato; instrument model MS-9 equipped with MS 50TC console and FAB source. The positive ion spectra are obtained from the samples dispersed in a few microliters of alpha-thioglycerol:diglycerol 1:1 bombarded with a 9 KeV beam of Xe atoms.

The experiment indicates a molecular weight of 1891 consistent with the structure assigned.

In an analogous experiment where *Nocardia orientalis* NRRL 2450 is replaced with *Streptomyces candidus* NRRL 3218 similar results are obtained.

4. Preparation of de-mannosyl teicoplanin complex component 5 (DM-TA2-5)

By operating with *Nocardia orientalis* NRRL 2450 as described in Preparation 1 but adding (after 48 hours from inoculum) as the substrate 200 mg of TA2-5 instead of TA2-2 a fermentation broth is obtained which is elaborated in the same manner as described under Preparation 1 above. The conversion yield in the fermentation broth is 36 percent. Recovery and purification are carried out by following the same procedure as in Preparation 1. The HPLC analysis performed under the same conditions as above shows RT values of 29.35 minutes for TA2-5 and of 30.92 minutes for DM-TA2-5 respectively. Yield 30 mg of pure DM-TA2-5 i.e. compound of formula (I) above wherein:

R = N-(9-methyl-decanoyl)-beta-D-2-deoxy-2-amino-glucopyranosyl;

$R_1$ = N-acetyl-beta-D-2-deoxy-2-amino-glucopyranosyl;

$R_2$=hydrogen.

The NMR spectrum of pure DM-TA2-5 recorded under the same condition of Preparation 1 shows the characteristics signals indicated in Table II.

The FAB mass spectrum recorded under the same conditions as described under Preparation 3 shows a molecular weight of 1891 which is consistent with the structure assigned.

In an analogous experiment where *Nocardia orientalis* NRRL 2450 is replaced with *Streptomyces candidus* NRRL 3218 similar results are obtained.

5. Preparation of de-mannosyl teicoplanin complex component 1 (DM-TA2-1)

By operating with *Nocardia orientalis* NRRL 2450 as described in Preparation 1 but adding (after 24 hours from inoculum) as the substrate 400 mg of TA2-1 instead of TA2-2 a fermentation broth is obtained which is elaborated in the same manner as described under Preparation 1 above. The conversion yield in the fermentation broth is 28 percent. Recovery and purification are carried out by following the same procedure as in Preparation 1. The HPLC analysis performed under the same conditions as above shows RT values of 22.58 minutes for TA2-1 and of 23.98 minutes for DM-TA2-1 respectively. Yield 55 mg of pure DM-TA2-1, i.e. compound of formula (I) above wherein:

R = N-(Z-4-decenoyl)-beta-D-2-deoxy-2-amino-glucopyranosyl;

$R_1$ = N-acetyl-beta-D-2-deoxy-2-amino-glucopyranosyl;

$R_2$ = hydrogen.

The FAB mass spectrum recorded under the same conditions as described under Preparation 3 shows a molecular weight of 1713 which is consistent with the structure assigned.

6. Preparation of de-mannosyl teicoplanin complex component 2 (DM-TA2-2)

A lyophilized tube containing *Nocardia orientalis* NRRL 2450 is open and aseptically transferred into a slant of oatmeal agar. After a 7 day incubation at 28° C., the culture is suspended in distilled water and inoculated into 2 Erlenmeyer flasks each containing 100 ml of vegetative medium S/bis having the following composition:

| | |
|---|---|
| Yeast extract | 4 g |
| Peptone | 4 g |
| Glucose | 10 g |
| MgSO4 | 0.5 g |
| KH2PO4 | 2 g |
| K2HPO4 | 4 g |
| Distilled water to | 1000 ml |
| pH after sterilization: | 7 |

The inoculated medium is incubated 48 hours at 28° C. on a rotary shaker at 200 rpm. The resulting culture, subdivided in several portions of 5 ml each, is frozen and stored for further use.

A portion of 2.5 ml of the frozen stock culture is used to inoculate a 500 ml Erlenmeyer flask containing 100 ml of vegetative medium S/bis. The culture was incubated at 28° C. for 48 h on a shaker at 200 rpm and 5 cm throw.

Five ml of this culture is used to inoculate 100 ml of productive medium C in a 500 ml flask having the following compositions:

| | |
|---|---|
| Glucose[a] | 2 g/l |
| Yeast extract | 5 g/l |
| Asparagine | 1.5 g/l |
| MgSO4 | 0.5 g/l |
| CaCO3 | 5 g/l |
| NaCl | 0.1 g/l |
| CaCl2.2H2O | 0.1 g/l |
| Mineral supplement[b] | 1 ml/l |
| pH after sterilization: | 6.9 |

[a]glucose was sterilized separately
[b]mineral supplement composition:

| | |
|---|---|
| Boric acid | 0.50 g/l |
| CuSO4.5H2O | 0.04 g/l |
| KI | 0.10 g/l |
| FeCl3.6H2O | 0.20 g/l |
| MnSO4.H2O | 0.40 g/l |
| FeSO4.7H2O | 0.40 g/l |
| Ammonium molybdate | 0.20 g/l |

Thirty flasks are prepared according to the procedure described above.

After 24 hours, the mycelium is recovered by centrifugation and washed twice in a saline isotonic solution (aqueous NaCl 1:1000 by weight) then resuspended in 3 l of physiological solution (the same volume of the productive medium) and 200 ml of substrate TA2-2 (i.e. teicoplanin complex component 2) are added to each flask and the fermentation is continued aerobically for 96 hours from the addition time. HPLC analysis of the fermentation broth shows a 35 percent conversion of TA2-2 to DM-TA2-2.

The whole reaction medium from all thirty flasks is brought to pH 10.5 by addition of 1 N NaOH and then filtered in the presence of a filter aid. The pH of the filtered broth is adjusted to 7.5 by adding 1 N HCl and 500 ml of Sepharose-epsilon-aminocapropyl-D-Alanyl-D-Alanine affinity resin (EPA Publ. No. 122969) are added thereto.

The mixture is stirred overnight at 4° C. The resin was then separated from the exhausted broth and poured into a chromatographic column. The column was washed with five resin volumes of Tris-HCl buffer (0.05 M, pH 7.5) and then with the same volume of Tris base solution (0.05 M). The resin is eluted with a solution of 1% ammonium hydroxide by collecting several fractions of 100 ml each. Fractions were neutralized with formic acid and analyzed by HPLC according to the conditions of Preparation 1.

Under the above conditions TA2-2 shows a retention time (Rt) of 24.71 min while DM-TA2-2 shows a RT of 26.30 minutes.

The fractions containing DM-TA2-2 are combined and then concentrated by ultrafiltration by using a 90 mm Hi-Flux U-F Cell Millipore apparatus supporting a PCAC Pellicon ultrafiltration membrane with a nominal molecular weight limit (NMWL) of 1000 dalton. The volume of the solution is reduced and the residual is lyophilized giving 2965 mg of crude DM-TA2-2.

The crude product is further purified according to the conditions of the Preparation 1 giving 880 mg of pure DM-TA2-2.

In an experiment, carried out under the same conditions as above but replacing the strain *Nocardia orientalis* NRRL 2450 with strain *Streptomyces candidus* NRRL 3218, similar results are obtained.

TABLE II

| Proton[***] | Multiplicity[*] | Teicoplanin complex (δ ppm) | DM-TA2-2 (δ ppm) | DM-TA2-3 (δ ppm) | DM-TA2-4 (δ ppm) | DM-TA2-5 (δ ppm) |
|---|---|---|---|---|---|---|
| various $CH_3$ groups | d | 0.84 | 0.83 | 0.84 | 0.84 | 0.84 |
| various $CH_2$ groups | m | 1.05–1.28 | 1.05–1.20 | 1.05–1.28 | 1.05–1.28 | 1.05–1.20 |
| $CH_2$ beta to C=O and isopropyl CH | m | 1.43 | 1.41 | 1.41 | 1.40 | 1.42 |
| acetyl group of glucosamine | s | 1.88 | 1.83 | 1.86 | 1.86 | 1.86 |
| $CH_2$ groups alpha to C=O | m | 2.03 | 2.00 | 2.02 | 2.01 | 2.00 |
| $C_2$—H of acetyl glucosamine | m | 3.33 | n.d. | n.d. | 3.31 | 3.35 |
| $CH_2$ of mannose | m | 3.48 | absent | absent | absent | absent |
| $C_2$—H of acyl glucosamines | m | 3.71 | n.d. | n.d. | 3.62 | 3.70 |
| x6 | dd | 4.10 | 4.12 | 4.12 | 4.13 | 4.12 |
| x5, x7, and anomeric H of acetyl glucosamine | d | 4.3–4.5 | 4.3–4.5 | 4.2–4.5 | 4.2–4.5 | 4.2–4.45 |
| x2 | m | 4.99 | 4.97 | 4.96 | 4.93 | 4.93 |
| 4f | s | 5.11 | 5.13 | 5.11 | 5.11 | 5.10 |
| x1[**] | s | 4.73 | 4.56 | 4.59 | 4.65 | 4.66 |
| anomeric H of mannose | s | 5.22 | absent | absent | absent | absent |
| z6 | s | 5.27 | 5.25–5.4 | 5.2–5.4 | 5.2–5.4 | 5.2–5.4 |
| x3 | d | 5.34 | 5.25–5.4 | 5.2–5.4 | 5.2–5.4 | 5.2–5.4 |
| anomeric H of acyl glucosamines | d | 5.40 | 5.25–5.4 | 5.2–5.4 | 5.2–5.4 | 5.2–5.4 |
| 4b | s | 5.56 | 5.53 | 5.53 | 5.51 | 5.51 |
| x4 | d | 5.64 | 5.65 | 5.68 | 5.69 | 5.68 |
| w6 | d | 6.22 | 6.09 | 6.08 | 6.09 | 6.09 |
| 3b, 3d, 3f | s | 6.3–6.5 | 6.25–6.5 | 6.2–6.4 | 6.25–6.4 | 6.25–6.4 |
| 7f | s | 6.50 | 6.28 | 6.29 | 6.29 | 6.29 |
| 7d | s | 6.71 | 6.39 | 6.35 | 6.38 | 6.38 |
| 1b | s | 6.74 | 6.62 | 6.65 | 6.62 | 6.60 |
| 5b | s | 7.09 | 7.26 | 7.18 | 7.18 | 7.17 |
| 6b | s | 7.78 | 7.84 | 7.83 | 7.83 | 7.83 | n.d. = not determined
[*] d = doublet; m = multiplet; s = singlet, dd = doublet of doublets.
[**] strongly influenced by pH
[***] the numbering of the atoms and rings is assigned as in the structure formula II

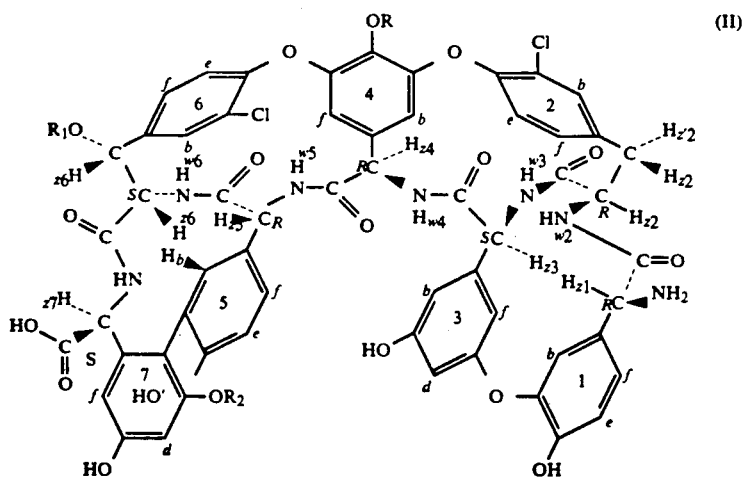

(II)

By examination of the relevant signals reported in the Table in comparison with those of teicoplanin complex it can be clearly deduced that the structures of the compounds DM-TA2-2, DM-TA2-3, DM-TA2-4 and DM-TA2-5 correspond to those of the teicoplanin complex major components lacking the mannosyl unit.

The key points for this conclusion can be evidenced by inspection of the table as follows. The characteristics signals at 3.48 and 5.22 for teicoplanin complex are absent in the de-mannosyl compounds. The variation of the signals of w6, 7f, 7d and 5b passing from teicoplanin complex to the de-mannosyl compounds reflects the different substitution at the ring 7. All the other signals practically are the same for teicoplanin complex and the de-mannosyl compounds.

We claim:

1. A process for the manufacture of a compound of the formula:

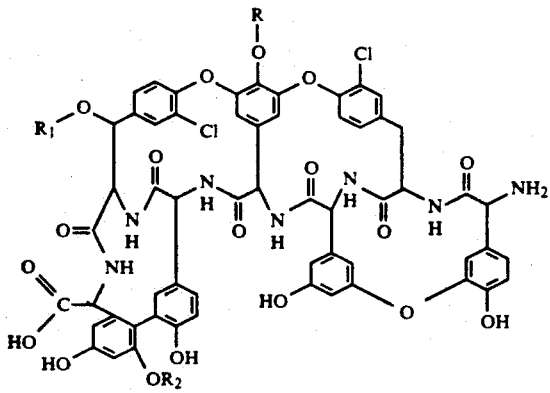

R is N-(Z-4-decenoyl)-beta-D-2-deoxy-2-amino-glucopyranosyl, N-(8-methyl-nonanoyl)-beta-D-2-deoxy-2-animo-glucopyranosyl, N-decanoyl-beta-D-2-deoxy-2-amino-glucopyranosyl, N-(8-methyl-decanoyl)-beta-D-2-deoxy-2-amino-glucopyranosyl, N-(9-methyl-decanoyl)-beta-D-2-deoxy-2-amino-glucopyranosyl;

$R_1$ is N-acetyl-beta-D-2-deoxy-2-amino-glucopyranosyl;

$R_2$ is hydrogen, their addition salts with acids and bases and any mixture thereof, in any proportion, which comprises submitting a substrate selected from teicoplanin complex, any mixture of the single components and a single component thereof to a microbiological transformation with a microorganism selected from Nocardia orientalis NRLL 2450 (ATCC 53630), Streptomyces candidus NRLL 3218 (ATCC 53629), the natural variants and mutants thereof exhibiting the same property of splitting the glycosidic bond with the D-mannose moiety in the teicoplanin molecule, the washed mycelium, and a cell free preparation thereof and recovering said substance or mixture of substances and, in case a mixture of substances is obtained, optionally separating it into its individual components.

2. A process of claim 1 wherein the microbial transformation is carried out by contacting the substrate with a growing culture of the above strains cultivated under submerged aerobic conditions in a medium containing assimilable sources of carbon, nitrogen and inorganic salts.

3. A process of claim 1 wherein is used a mycelium of the above identified de-mannosylating microorganism culture, washed in an isotonic saline solution.

* * * * *